United States Patent [19]

Grieshaber

[11] Patent Number: 4,947,871
[45] Date of Patent: Aug. 14, 1990

[54] PROCESS THE SURGICAL CORRECTION OF AMETROPIA OF ONE OR BOTH EYES OF LIVING BEINGS

[75] Inventor: Hans R. Grieshaber, Schaffhausen, Switzerland

[73] Assignee: Grieshaber & Co. AG Schaffhausen, Schaffhausen, Switzerland

[21] Appl. No.: 220,803

[22] Filed: Jul. 18, 1988

[30] Foreign Application Priority Data

Aug. 10, 1987 [CH] Switzerland ............................ 3056/87

[51] Int. Cl.$^5$ ................................................ A61F 9/00
[52] U.S. Cl. ..................................... 128/898; 606/107; 606/161
[58] Field of Search ..................... 128/305, 305.1, 898; 606/107, 161, 166

[56] References Cited

U.S. PATENT DOCUMENTS

| | | | |
|---|---|---|---|
| 4,173,980 | 11/1979 | Curtin | 128/303 R |
| 4,205,682 | 6/1980 | Crock et al. | 128/305 |
| 4,526,171 | 7/1985 | Schachar | 128/305 |
| 4,796,623 | 1/1989 | Krasner et al. | 128/305 |

Primary Examiner—Michael H. Thaler
Assistant Examiner—William Lewis
Attorney, Agent, or Firm—Helfgott & Karas

[57] ABSTRACT

A process and an apparatus for the surgical correction of ametropia, which can occur as a function of the corneal curvature in the optical system of one or both eyes of living beings, are proposed. The apparatus includes a grinder essentially comprising a base member to be fixed to the eye and a rotary-driven grinding or polishing punch. A displacement of the focal point in the retinal plane is achieved and consequently the ratio of the optical axis to the refractive force of the eye is corrected by grinding and/or polishing the cornea surface in the optical curvature region.

3 Claims, 2 Drawing Sheets

PROCESS THE SURGICAL CORRECTION OF AMETROPIA OF ONE OR BOTH EYES OF LIVING BEINGS

BACKGROUND OF THE INVENTION

The invention relates to a process and an apparatus for the surgical correction of defective vision or ametropia, particularly that of one or both eyes of living beings, dependent on a corneal curvature in the optical system.

In objective refraction determination (refraction state of one or both eyes) use is made of the fact that in the optical system in the case of an emmetropic or orthoscopic eye the curved cornea and the natural lens essentially refract the parallel incident light beams, so that the focal or intersection point thereof is in the retinal plane. However, if there is a disparity between the refractive force and the axial length of the optical system, then ametropia occurs, whilst in the case of a short-sighted or myopic eye the focal point is in front of the retina and in the case of a far-sighted or hyperopic eye the focal point is behind the retina. If the incident light beams do not form a common focal point (astigmatism), then the curvature of the cornea varies in different directions, so that a so-called distortion occurs.

The primary correction means for such ametropia are essentially spectacles, contact lenses, etc. In the case of extreme ametropia, it is also known to bring about a correction by surgery, e.g. making use of keratoplasty, keratophakia, epikeratophakia, or keratomileusis modifiying the corneal curvature and thereby bringing about a displacement of the focal point of the retina. According to another operative correction process for less severe cases of ametropia, several radial cuts are made in the periphery of the cornea, so that the latter loses curvature radius and therefore has a smaller refractive force. This operative method known as "radial keratotomy" is limited to the myopic eye.

In the aforementioned, traumatic correction processes, the cornea is on the one hand significantly weakened due to the depth of the radial cuts to be made and on the other hand it is not possible to exclude a gradual redevelopment to the preoperative curvature radii of the cornea and consequently a return of the myopic, hyperopic or astigmatic state of the eye.

SUMMARY OF THE INVENTION

It is an object of the present invention to provide a process and an apparatus for performing the process, by means of which the myopia, hyperopia or astigmatism caused by the corneal curvature can be corrected on a new corneal curvature located in the vicinity of the optical zone of the cornea.

In the process according to the invention, for a displacement of the focal point into the retinal plane correcting the ratio of the optical axis to the refractive force, the cornea undergoes grinding and/or polishing in its optical curvature region.

The apparatus for performing the process according to the present invention comprises a base member to be fixed detachably to the eye and a grinder insertable in the base member, said grinder comprising a grinding or polishing punch drivable in rotary manner and which is provided in the side facing the corneal surface of the eye with a grinding surface constructed in accordance with a correction radius.

Further features of the invention can be gathered from the following description in conjunction with the drawings:

DETAILED DESCRIPTION OF THE PREFERRED EMBODIMENT

Figures 1, 3:
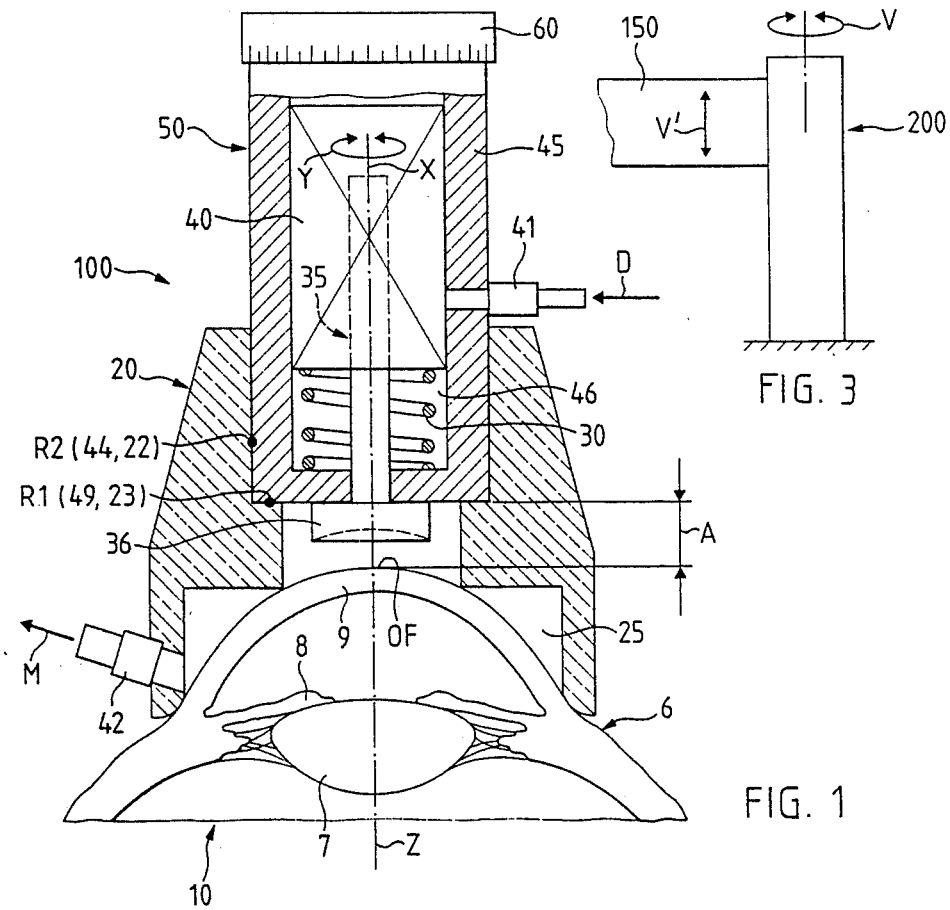
FIG. 1 is a sectional view through a cornea grinding apparatus according to the invention.
FIG. 3 is a partial schematic side view showing a modified support of the cornea grinding apparatus on the beam of the standard.

FIG. 1 shows an embodiment of a cornea grinding apparatus shown on larger scale and in a simplified sectional view. The grinding apparatus is designated overall at 100 and is constructed for the correcting curvature change of the cornea of a living being or organism. The grinding apparatus 100 essentially comprises a grinder 50 and a base member 20, which is used, on the other hand, for receiving the grinder 50 and, on the other hand, for the strict, sterile fixing to the eye 10, which is diagrammatically shown in FIG. 1.

In the case of eye 10, which is only partly shown and on a larger scale, 9 is the cornea acting as the optical window of the eye, 8 is the iris acting as the diaphragm of the eye, 7 is the lens acting as a dioptric member and 6 is the conjunctiva. Cornea 9 which is shown as a single layer in FIG. 1 is in reality a 5-layer tissue comprising a relatively thin, surface corneal epithelium with a basal membrane, a relatively thin Bowman's membrane below it, the corneal stroma forming most of the cornea, the Descenet's membrane and above same a relatively thin endothelial layer whilst, considered towards the anterior cavity of the eye, to the Descenet's membrane and endothelial layer are connected to the corneal stroma. The 5-layer corneal tissue is transparent and has a certain elasticity.

Grinder 50 essentially comprises a casing 45 shown partly in section and in which is arranged a drive member 40, a grinding or polishing punch 35 drivable by the drive member 40 rotated about a vertical axis X in arrow direction Y and a restoring spring 30. For receiving parts 30, 35 and 40, casing 45 is provided with a correspondingly constructed recess 46. At an upper end of the casing 45 is provided a setting member, preferably a micrometer screw 60, whose function will be described hereinafter, and fixing of the parts together takes place with non-shown suitable means.

It is pointed out that the drive member 40 for the grinding or polishing punch 35 can e.g. be a high-speed air turbine, a direct current motor, a stepping motor or an external drive (not shown), whereby when using an external drive the latter is in operative connection by means of an additional shaft with the grinding or polishing punch 35. In the exemplified embodiment, the drive member 40 is a per se known, diagrammatically shown turbine operating at a speed of 250,000 revolutions per minute and which is supplied with compressed air entering a connecting piece 41 arranged on the casing 45 in the direction of arrow D.

Figure 2:
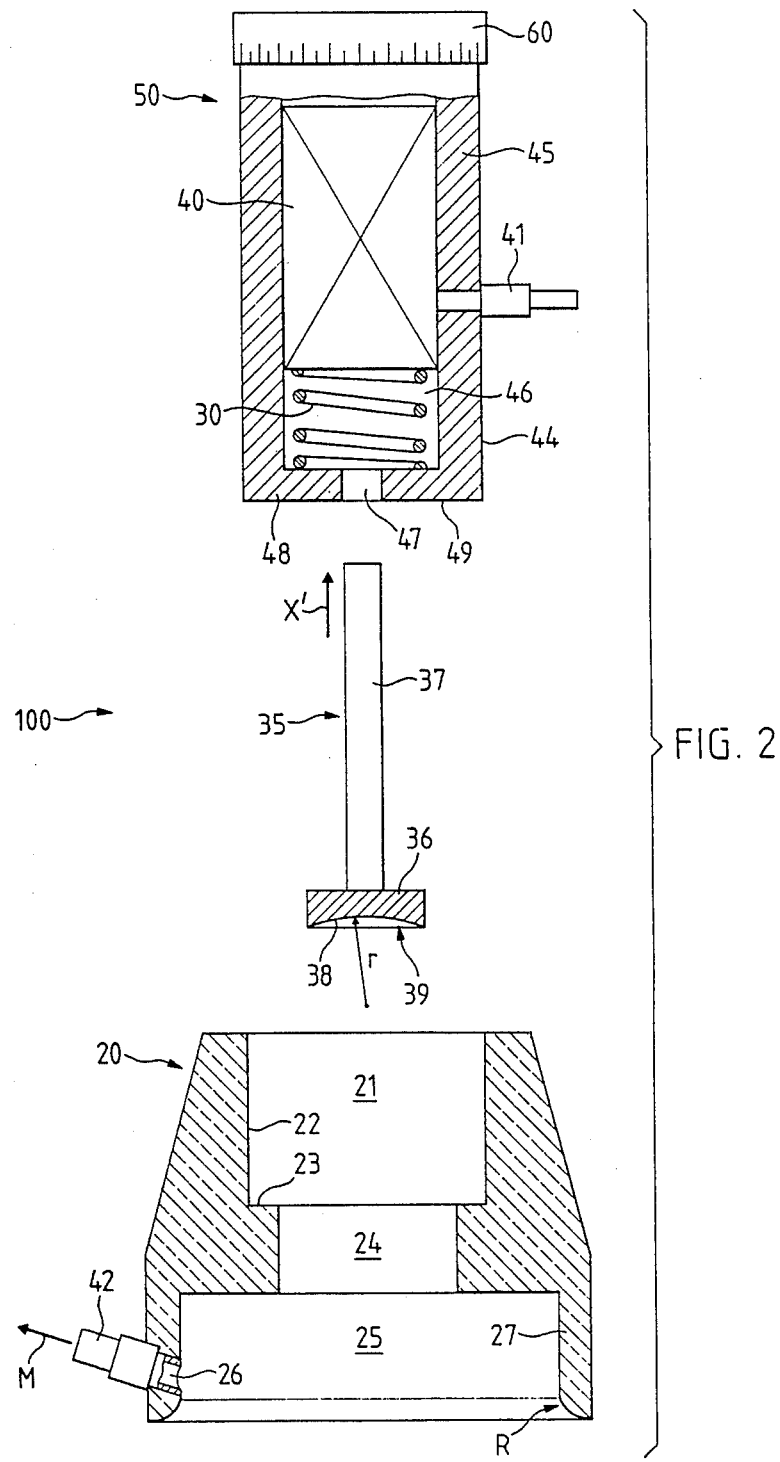
FIG. 2 is a sectional exploded view of the grinding apparatus according to FIG. 1.

FIG. 2 shows an exploded view of the cornea grinding apparatus 100, which includes the grinder casing 45, the grinding or polishing punch 35 and the base member 20, whereby parts 45, 35, and 20 will be described in greater detail hereinafter.

As has already been stated, for receiving the turbine 40, casing 45 is provided with the recess 46 and in the upper area is constructed for receiving the micrometer screw 60. In the lower area, casing 45 has a base 48 formed with a bore 47. An outer face 49 of case 48 serves as a reference face 23 of the base member 20.

The grinding or polishing punch 35 has a shaft 37, on which is arranged, preferably by shaping at one end thereof, a dish-shaped punch disk 36. The sectionally shown punch disk 36 is provided on the underside 39 with a substantially concave surface 38, whose specific shaping and size will be described hereinafter. It is provided with a fine-grain crystalline and preferably diamond dust covered surface structure, the diamond crystal size being selected in such a way that a corresponding grinding or polishing action for the inventive process is obtained The grinding or polishing punch 35 insertable in the direction of arrow X' (FIG. 2) into both the casing 45 and turbine 40 and preferably centered on the bore 47, is operatively connected in a non-shown manner in the assembled state (FIG. 1) via the shaft 37, to the turbine 40 and is driven by the same in the direction of arrow Y for the grinding or polishing process. The non-rotary, operative arrangement of the grinding or polishing punch 35 in the turbine 40 is such that a rapid replacement without additional auxiliary means is ensured.

The base member has a first recess 21, a second recess 24 and a third recess 25. The third recess 25, after fixing the basic member 20 to eye 10, forms a vacuum space, which is connected by means of an opening 26 to a suction connection 42. For an optimal sealing engagement of wall 27 of vacuum space 25 in the vicinity of the conjunctiva 6, wall 27 is provided on its inside with a radius R. The first recess 21 serves to receive the complete grinder 50, whose lower casing region 44 in the assembled state (FIG. 1) is centered and guided on a side wall 22, whilst the lower face 49 of the casing 45 rests on the annular surface 23 of the base member 20. Base member 20 is made from a readily sterilizable material, preferably a transparent material, such as transparent plexiglass or the like. In the assembled position, in which grinding apparatus 100 is fixed to the eye 10 (FIG. 1) the two surfaces 49,23 of the parts 20,45 serving as a support act as an axial reference R1 with respect to the corneal surface OF and the two cylindrical walls 44,22 of parts 20,45 as a radial reference R2 with respect to the optical axis only precisely definable in a diagrammatically represented eye and running from the vertex of the cornea to the posterior pole of the eye (not shown).

The inventive process for the surgical correction of the ametropia dependent on the corneal curvature comprises the essential process steps as follows:

Step 1: Establishing the refraction (refractive spate) of the ametropic eye by means of a known per se refraction method.

Step 2: Determination of the corneal curvature by means of a correspondingly constructed opthalmometer from which it is preferably possible to directly read the corneal curvature radius dependent on various quantities.

Step 3: Calculation of the necessary correction value, i.e. the correction radius, taking into account the corneal curvature determined by means of step 2.

Step 4: Calculation of the grinding depth taking into account the parameters determined in steps 2 and 3, i.e. whilst taking into account the preoperative corneal curvature and the correction radius calculated in step 3.

Step 5: Determining the optical center Z of the cornea 9 and a precisely central mounting and fixing of the base member 20 to the eye 10.

Step 6: Determining the distance A from the reference face R1 to the cornea surface OF.

Step 7: Adjusting the micrometer screw 60 to the grinding depth, calculated by means of step 4, plus the offset or distance A determined by means of step 6.

Step 8: Selection of the correspondingly constructed (correction radius according to step 3) grinding or polishing punch 35, insertion in grinder 50 and sterilizing the complete grinder.

Following on to the above steps 1 to8, which essentially constitute a preparatory phase, the actual operation now takes place on the cornea surface OF under absolutely sterile conditions, in such a way that the grinder 50 is inserted in the recess 21 of the base member 20 and subsequently the grinding or polishing punch 35 is driven at the corresponding speed and is supplied with the parameters concerning the cornea surface grinding or polishing process determined by means of steps 2, 3 and 4. The micrometer screw 60 provided on grinder 50 ensures in a non-conventional shown manner a highly accurate feed movement of the grinding or polishing punch 35, which is limited by a non-shown stop. Whilst taking account of the determined parameters, during the grinding or polishing operation, i.e. during the actual operation, the first relatively thin cornea epithelial layer, including the Bowmann's membrane and part of the corneal stroma are removed, the exposed corneal stroma being overgrown again by epithelial cells after a certain time.

In the case of the grinding apparatus 100 shown in FIG. 1 the base member 20 with the fitted grinder 50 is held on the eye 10 using non-conventional shown means, such as individual elements made relatively small with a low weight, but without impairing the necessary stability.

The detachable fixing of the base member 20 to the eye 10, by circular manner round the cornea or in the external region of the eye can take place by sewing, clips or the like. In the exemplified embodiment, the base member 20 is held superficially to the conjunctiva 6 of the eye 10 by producing a vacuum in space 25. For this purpose a vacuum is produced in space 25 by known but non-shown means and via the suction connection 42, and this condition is maintained during the operation.

In the case of the grinder 50 the grinding or polishing punch 35 is constructed as a so-called rising spindle, which in the fitted state performs the feed movement towards the cornea surface OF, as well as the rotary movement. However, as diagrammatically shown in FIG. 3, the possibility also exists of detachably placing the grinder 50 on a partly shown beam 150 of a standlike standard or post 200, which can be pivoted away in arrow direction V and vertically adjustable in arrow direction V'. In this modification, the grinder 50 together with the grinding or polishing punch 35 is fed to the cornea surface OF in readily reproducible manner, the punch 35 only performing the rotary movement.

In the case of the above-described high-speed grinding technology, cooling may be necessary during surgery. A suitable medium is e.g. a viscoelastic substance, which is supplied by means of a non-shown circulation duct system to the grinding or polishing punch 35 in the vicinity of the punch disk 36 and can be sucked away by means of the connecting piece 42 in the direction of arrow M.

As stated, the replaceable grinding or polishing punch 35 is provided on the underside of the punch disk 36 with the concave surface 38 acting as a grinding surface on the particular cornea surface OF during rotation. Due to the fact that the corneal radius of curvature naturally differs between the individual eyes, for the inventive correction of ametropia of the individual eye, it is necessary to provide corresponding curvature radii r of the concave surface 38. The particular radius of curvature r is approximately 5 to 15 mm, preferably 6.5 to 12 mm with a grading of 1/10 mm. The choice of the grinding or polishing punch 35 to be used is a function of the values calculated or determined by means of steps 2, 3 or 4 (corneal curvature, correction value, grinding depth).

An important factor in the choice of the grinding or polishing punch 35 to be used is that the ratio of a grinding depth to a grinding diameter is chosen in such a way that following the grinding or polishing away of the exposed cornea surface OF, which is subsequently overgrown again by the epithelial cells, the smooth surface necessary for the desired optimum vision function of the individual eye is provided.

As a result of the necessary comprehensive selection of interchangeable grinding or polishing punches 35, the possibility exists of constructing same in two-part manner, comprising shaft journal 37 and punch disk 36 and to merely replace the disk which is provided with the corresponding concave surface 38, fixing same by not shown means.

What is claimed is:

1. Process for the surgical correction of ametropia, particularly such ametropia in the optical system of one or both eyes of living beings, which is dependent on a corneal curvature, comprising the following steps:
    (a) determining the refraction of the individual ametropic eye;
    (b) determining a corneal curvature of the eye;
    (c) calculating a correction radius (r) of the corneal curvature from a value of the corneal curvature determined in the step (b);
    (d) calculating a grinding depth, whilst taking into account the corneal curvature and correction radius (r) determined in the steps (b) and (c);
    (e) determining the optical center (Z) of the cornea; and
    (f) grinding or polishing the cornea in its optical curvature region for a displacement of the focal point in the retinal plane correcting the ratio of the optical axis to the refractive force.

2. Process according to claim 1, wherein during said grinding or polishing step, the cornea surface or a grinding member is cooled with a suitable cooling medium.

3. Process according to claim 2, wherein said suitable cooling medium includes visco elastic substances.

* * * * *